United States Patent [19]

McDonald

[11] Patent Number: 4,813,957

[45] Date of Patent: Mar. 21, 1989

[54] INTRAOCULAR LENS IMPLANTATION

[76] Inventor: Henry H. McDonald, 65 N. Madison, Ste. 810, Pasadena, Calif. 91101

[21] Appl. No.: 42,881

[22] Filed: Apr. 27, 1987

[51] Int. Cl.$^4$ .............................................. A61F 2/16
[52] U.S. Cl. ...................................................... 623/6
[58] Field of Search ............................................ 623/6

[56] References Cited

U.S. PATENT DOCUMENTS 1,837,277  12/1931  Lund ................................. 128/321
4,573,998  3/1986  Mazzocco ........................... 623/6

FOREIGN PATENT DOCUMENTS 2555952  6/1985  France .

Primary Examiner—V. Millin
Assistant Examiner—James Prizant
Attorney, Agent, or Firm—William W. Haefliger

[57] ABSTRACT

Intraocular lens implantation is achieved via a very small incision in the corneo-scleral limbus of the eye.

4 Claims, 4 Drawing Sheets

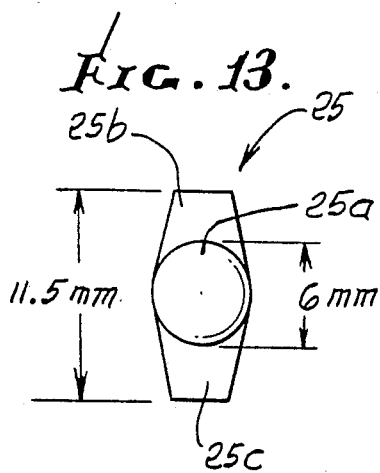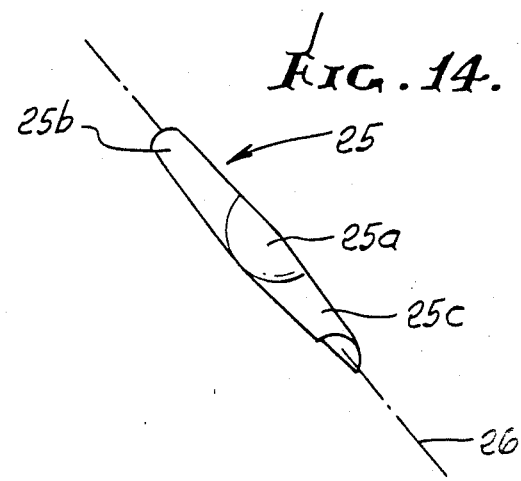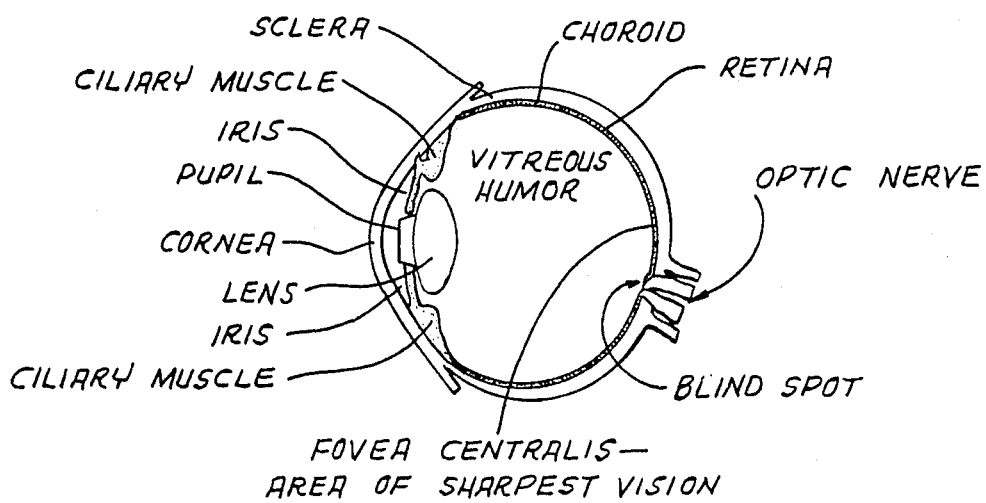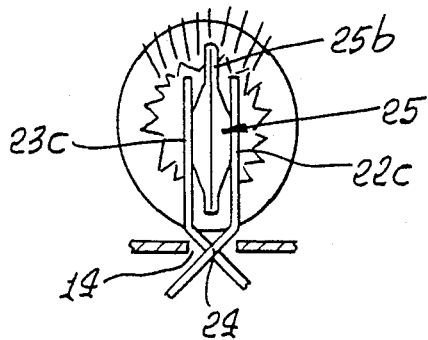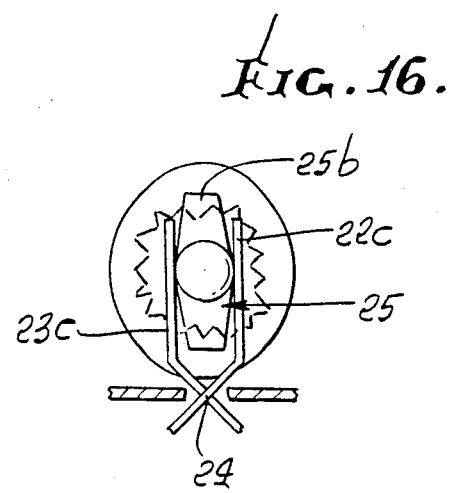

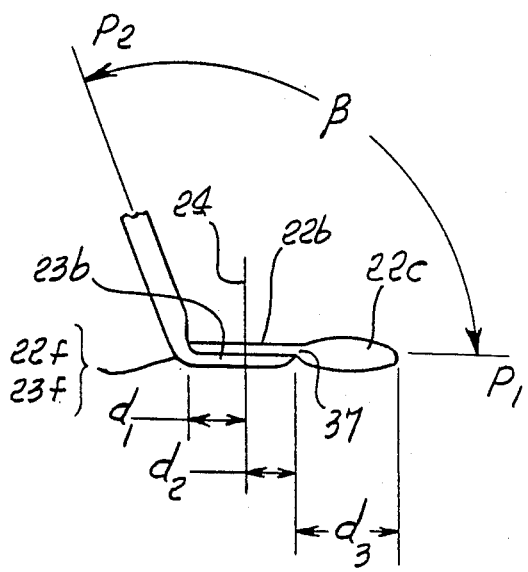
Fig. 18.
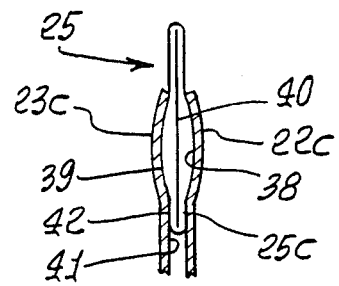
Fig. 19.
Fig. 20.

INTRAOCULAR LENS IMPLANTATION

BACKGROUND OF THE INVENTION

This invention relates generally to intraocular lens implantation, and more particularly concerns apparatus and method for achieving such implantation via a very small surgical incision in the corneo-scleral limbus of the eye.

In the past, forceps have been used with blades that clamp the plastic lens for introducing it into the eye via a relatively wide wound or incision in the corneo-scleral limbus. A typical wound was required to have a width of about 7-15 millimeters in order to pass the forcep blades and to allow spreading of the blades to release the plastic lens in the eye.

Problems encountered included laceration of the elastic silicon lens, and undesirable sudden release and rapid unfolding of the lens (as opposed to gentle release) causing injury to intraocular tissue, due to inability to separate the blades widely and gently. The usual wide incision is undesirable due to the amount of suturing required to close the wound, and time required for such suturing, increased or undesirably long convalescence time, increase in astigmatic complications, difficulty in preventing collapse of the intraocular chambers during the operation, and increased risk of post-operative complications. Further, plastic lenses could and did at times become captured by the blades of prior forceps, requiring dangerous instrumentation to release the lens from the grasp of such forceps.

SUMMARY OF THE INVENTION

It is a major object of the invention to provide method and apparatus, overcoming the above problems and difficulties. Basically the invention permits wide separation of the blades and gentle release of the folded lense within the eye, while motion is transmitted to the blades via a very narrow incision.

The method involves implanting a plastic lens into the eye lens zone from which a natural but cataractous lens has just been removed (or removed in the past) as via a narrow surgical incision in the corneo-scleral limbus, and while using a forceps having blades projecting from or beyond cross arm portions defining a crossover locus. The method includes the steps:

(a) manipulating the forceps to introduce the blades and clamped plastic lens through the incision and into said zone, and to place the cross arm portions in said incision, (b) further manipulating the forceps to spread the blades thereby releasing the plastic lens to accommodate to said zone, and thereafter relatively closing together the blades while maintaining the cross-fixation arm portions at or proximate said incision, (c) and withdrawing the relatively closed together blades from said zone and via said incision.

Typically, the (b) step is carried out to separate the blades to an extent much wider than the incision; and the blades are, for example, separated within the eye to an extent in excess of 4mm, and typically between 6-8mm, the narrow surgical incision having a width less than about 3mm.

Further, the plastic lens is typically folded and held in elastically folded state, by the blades, while being introduced through the narrow incision; and the blades are slowly and gently spread apart, by pressure on the forceps handles producing motion transmission through the narrow incision, to allow controlled elastic unfolding of the lens for precision interfitting with the eye tissue. Such full excursion blade separation is achieved by force transmission through the cross fixation arm portions which in the wound do not require more than 1 to 2 mm space or size.

Finally, the improved forceps is not only useful as an intraocular lens holder, but also as a utility forceps, capable of passing through a small puncture wound to insert a lens implant, or grasp an intraocular foreign body for its removal or better positioning—all through the small puncture wound.

These and other objects and advantages of the invention, as well as the details of an illustrative embodiment, will be more fully understood from the following specification and drawings, in which:

DRAWING DESCRIPTION

FIG. 13 is enlarged frontal view of a plastic lens of the type to be implanted;

FIG. 14 is a perspective view of the FIG. 13 lens, partially folded;

FIG. 15 is a frontal view of the forceps of the invention with blades holding the plastic lens in folded condition and positioned within the eye, as related to the lens capsule;

FIG. 16 is a view like FIG. 15, after the blades have been separated, showing elastic expansion of the plastic lens between the separated blades, with no remaining dangerous elastic compression, and as dimensionally related to the narrow incision.

FIG. 17 is a schematic view of the eye; and

FIGS. 18-20 are views showing modifications.

DETAILED DESCRIPTION

Figure 1:
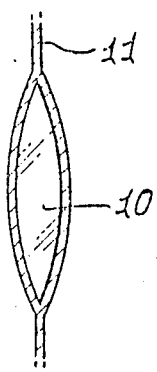
FIG. 1 is a side view of a cataractous opaque lens.
Figure 2:
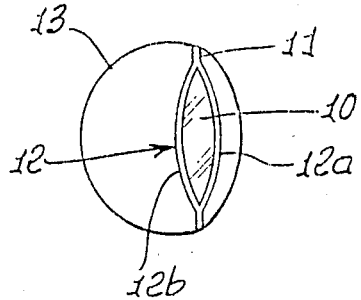
FIG. 2 is a side view of the cataractous opaque lens within the lens capsule in the eye.
Figure 3:
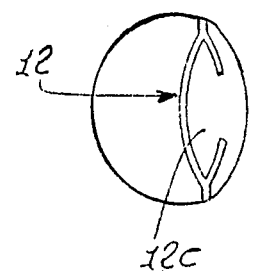
FIG. 3 is a side view of the anterior lens capsule after removal of the opaque cataract lens and the central portion of the anterior capsule.
Figure 4:
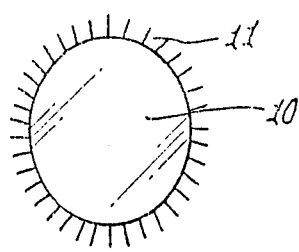
FIG. 4 is a front view of the cataractous lens as seen in FIG. 1, showing zonula fibers holding the capsule.

Referring first to FIGS. 1 and 2, they show, in side view, and schematically, a cataractous opaque lens 10, bounded peripherally by zonula fiber 11, and located between anterior and posterior portions 12a and 12b of the lens capsula. The eye outline appears schematically at 13, and FIG. 17 is a section accurately showing corresponding parts, as well as other parts, of the eye. FIG. 3 shows the capsule void 12c after removal of the cataractous lens tissue. FIG. 4 is a front view of the lens 10 seen in side view in FIG. 1.

Figure 5:
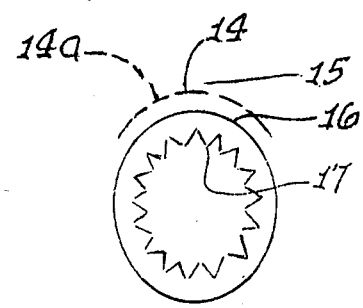
FIG. 5 is a front view showing the location of a surgical 1 to 2mm incision in the corsoscleral tissue, outwardly from the limbus.

FIG. 5 is a schematic frontal view of the eye, showing a narrow (for example about 3mm wide) incision or puncture 14 in the corneoscleral tissue 15, at a short distance (as for example about 2mm) from the limbus 16, the latter designating the merging of light (scelera) and dark (iris periphery) zones of the eye. The present invention makes possible the use of such a narrow, i.e. short, puncture wound, as opposed to the prior very wide incision, indicated by broken lines 14a, which was necessary in order to implant a plastic or silicon lens into the capsula 12. Such a wide (typically 15-18mm) incision requires much more suturing than is required for the short incision or puncture wound 14, and requires a longer convalescence period, with increased risk of post-operative complications. The cataractous lens is more recently removed by phacoemulsification with ultrasonic vibration fragmentation and aspiration via the puncture 14, leaving jagged anterior "leaves" or serrations 17 in the anterior capsula portion 12a; the posterior capsula portion 12b remains clear. Anterior capsulatomy removes the central anterior capsula, leaving space indicated at 12c in FIG. 3.

Figure 6:
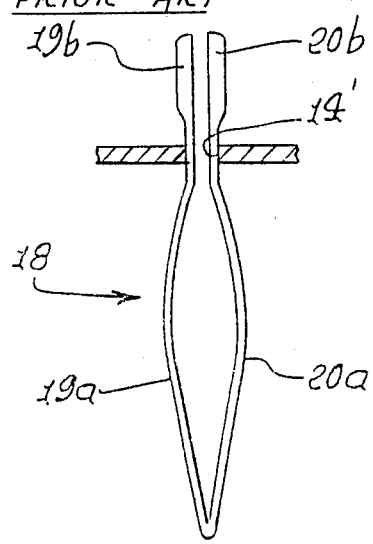
FIG. 6 is a front view showing prior straight forceps with arms and blades whose narrow separation is limited by a 3mm incision in the corsoscleral limbal tissue.

FIG. 6 shows a straight forceps 18 having an arm 19a continuing forwardly to merge with a blade 19b, and an arm 20a continuing forwardly to merge with a blade 20b. The blades have been inserted through a narrow (3mm for example) incision as indicated at 14', and that incision characteristically severely limits the separation of the blades to release a plastic or silicon lens clamped between them; for that reason, it was previously considered necessary to form a wide incision, as previously referred to at 14a, in order to release the plastic replacement lens. Such a large wound tends to allow fluid escape from the eye, with impending ocular collapse and damage in the intraocular tissue.

Figure 7:
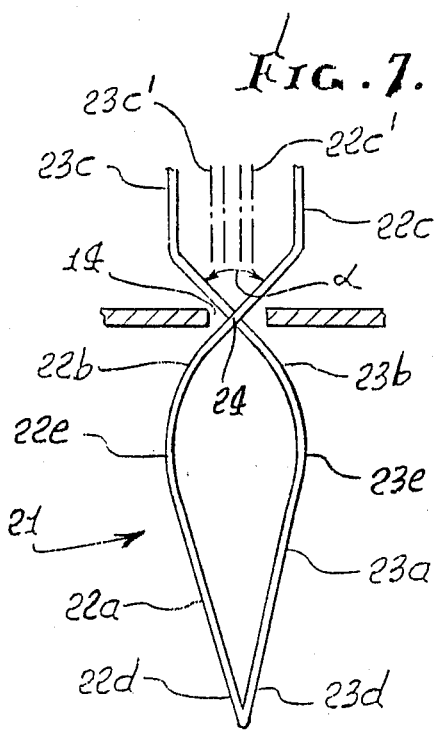
FIG. 7 is a front view showing the forceps of the invention with cross action arm portions passing through the corsoscleral limbal tissue, the forceps blades having been widely separated, i.e. not limited as in FIG. 6.

The forceps of the present invention is shown schematically at 21 in FIG. 7. That forceps is characterized by an arm 22a extending generally forwardly to merge with diagonally rightwardly and forwardly extending cross-over portion 22b, the latter terminating at blade 22c. Similarly, a second arm 23a extends generally forwardly to merge with diagonaly leftwardly and forwardly extending cross-over portion 23b, the latter terminating at forwardly extending blade 23c parallel to blade 22c. The blades also extend forwardly relative to the diagonals. Note that the cross-action portions 22b and 22c are laterally displaced and slide adjacent one another by sequence or release manipulation of the forceps arms so that the cross-over point 24 remains in, or very closely proximate to, the puncture locus 14, as during expansion of the blades from their initially inserted broken line positions 22c' and 23c' to their expanded solid line positions 22c and 23c. This then allows a wide degree of such expansion to free the plastic lens within the capsula 12, without restriction imposed by the narrow puncture 14. Arms 22 and 23 defining handles 22e and 23e are typically joined together at their outer ends 22d and 23d.

FIGS. 8-12 show the implantation sequence for an elastic, molded plastic or silicon lens implant 25 as represented in FIG. 13. That lens has an intermediate and bead-like optical portion 25a, and two oppositely extending haptics or tangs 25b and 25c. It is foldable about a lengthwise axis 26, as seen in FIG. 14, so as to be clamped or held between the blades 22c and 23c, as during implantation viewed in FIG. 8 and 9, and via the narrow (about 3mm or less) puncture 14. Typical dimensions appear in FIGS. 13 and 14.

Figure 8:
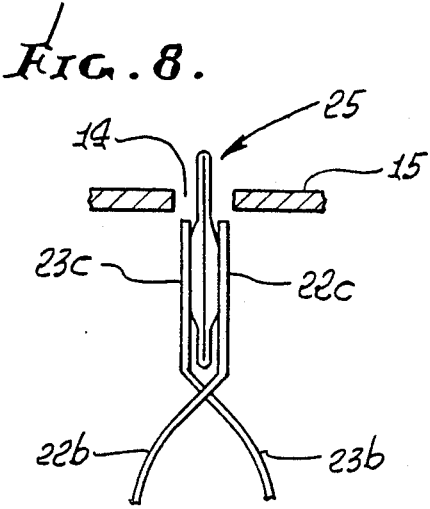
FIG. 8-12 are sequential views showing steps in the intraocular implantation of a plastic lens, using the forceps of the present invention.
Figure 9:
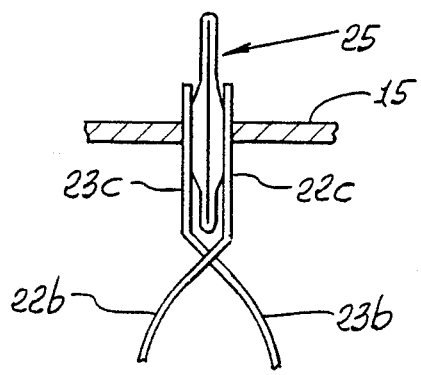
Figure 10:
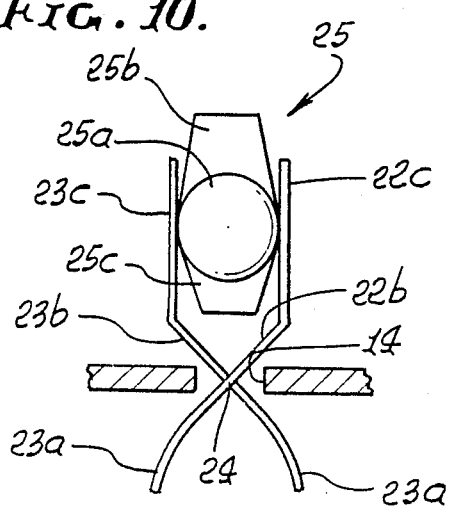

In FIGS. 8 and 9 the arm cross-over (cross-fixation) point or locus 24 is very close to the blades, whereby the blades are held near one another, with the folded lens therebetween, for insertion through the narrow puncture. Once insertion is completed, characterized by location and retention of the forward tang 25b into the tissue bounding the lens cavity or void, as seen in FIG. 15, the blades are allowed to slowly separate as by slow release of manual pressure on the bowed spring arms 22a and 23a of the forceps, and the forceps is also manipulated slightly lengthwise (forward or backward) to maintain the cross-over point 24 in, or proximate, the puncture 14. This allows ultimate wide separation of the blades, to between 4 to 6 mm, as seen in FIGS. 10 and 16, without restriction imposition by the small narrow puncture. The width of the puncture is less than about 3mm. Note that the cross-over point 24 has moved away from the blades in FIGS. 10 and 11. Angle α defined by the portions 22b and 23b is between 75° and 105°. The blades remain approximately parallel during their excursions.

Figure 11:
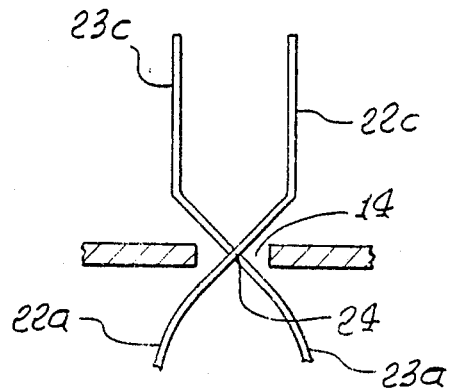
Figure 12:
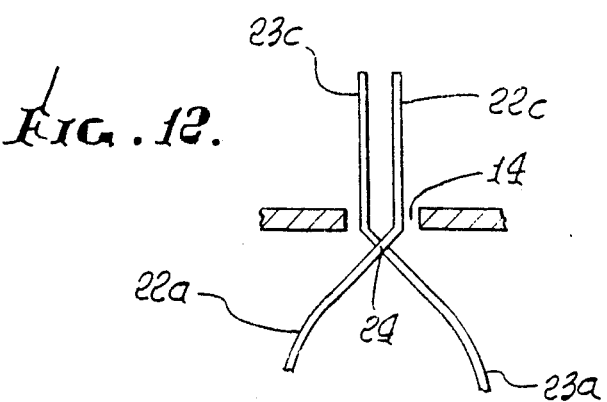

In FIG. 11, the elasticaly expanded (unfolded) artificial lens has dropped away from between the blades, leaving them free for relative closure, as seen in FIG. 12. In the latter, the cross-over point 24 has moved relativley back toward the blades; the blades are closed together and they are positioned for retraction through the puncture.

As referred to above, the forceps of the present invention, has utility, not only as an intraocular lens holder but also as a utility forceps, capable of passing through a small puncture wound to insert a lens implant, or grasp an intraocular foreign body for its removal or better positioning, all through the small puncture wound.

The specific angulations of the cross fixation arm portions, their lengths, and the sizes of the two blades, as related to the narrow puncture wound, may vary somewhat depending upon the specific use and functioning of the forceps.

In FIG. 18, the blades 22c and 23c and the cross over portions 22b and 23b of the arms define a first plane $P_1$ and the remainders of the arms 22a and 23a define a second plane $P_2$. The angle β between $P_1$ and $P_2$ is between 100° and 130°. Arms 22a and 23a join the diagonals at elbows at 22f and 23f. The cross-over locus appears at 24. The dimension $d_1$, 22f to 24 is about 4mm; the dimension $d_2$ from 24 to the blade inner end 37 is about 3mm; and the dimension $d_3$, which is the blade length, is about 6mm.

In FIG. 19, each blade 22c and 23c has a shallow concave inner surface 38 to match (or approximately match) the surface convex curvature 39 of the plastic molded lens 25 held folded in half at 40. Each blade also has a second inner surface 41 which is approximately flat to match the flat outer surface 42 of the folded haptic 25c.

In FIG. 20, at least one of the diagonal portions, such as arm portion 23b, has an interior, lengthwise extending, irrigation channel or annula 43, for passing eye irrigating liquid to outlet 44, in the eye, when the blades are located in the eye. Passage 45 in arm 23a feeds liquid to channel 43, and under pressure sufficient to keep the anterior and posterior chambers in the eye from collapsing.

I claim:

1. The method of intraocular implantation of a plastic lens in the eye lens zone from which a natural lens has been removed via a surgical incision in the corneo scleral limbus, the method employing a surgical forceps having blades projecting beyond cross-over arm portions defining a cross-over locus, the blades clamping the plastic lens to be implanted, said method including the steps:

(a) folding the plastic lens into flattened U-shape and effecting clamping of the folded lens by the blades, and then manipulating the forceps to introduce the blades and folded and clamped plastic lens through said incision and into said zone, and to locate said cross-over locus at or closely proximate said incision, (b) thereafter further manipulating the forceps to spread apart the blades thereby releasing the plastic lens by unfolding to accomodate to said zone while maintaining the cross over locus at or proximate the incision, and thereafter relatively closing together the blades while continuing to maintain the cross-over locus at or proximate said incision, (c) and withdrawing the relatively closed together blades from said zone and via said incision, (d) said spread apart of the blades being carried out to separate the blades over their entire lengths to an extent wider than the width of the incision, the blades being separated to an extent in excess of approximately 7mm, and said incision having a width of approximately 3mm, or less.

2. The method of claim 1 wherein said releasing of the plastic lens is carried out to allow elastic unfolding of the folded lens within said zone.

3. The method of claim 1 wherein said manipulating of the forceps to spread apart the blades includes displacing the forceps generally lengthwise to maintain the cross-over locus in the incision as the blades are spread apart.

4. The method of claim 1 wherein said folding of the lens is carried out to fold the entire lens into two adjacent sections extending in substantially parallel planes.

* * * * *